(12) United States Patent  
Jones et al.

(10) Patent No.: US 9,198,943 B2
(45) Date of Patent: Dec. 1, 2015

(54) SILENE CAPENSIS FOR INHIBITING CRAVINGS

(71) Applicants: Michael Parker Jones, Salt Lake City, UT (US); Jonathan Michael Benns, Salt Lake City, UT (US); David Allan Jones, Salt Lake City, UT (US)

(72) Inventors: Michael Parker Jones, Salt Lake City, UT (US); Jonathan Michael Benns, Salt Lake City, UT (US); David Allan Jones, Salt Lake City, UT (US)

( * ) Notice: Subject to any disclaimer, the term of this patent is extended or adjusted under 35 U.S.C. 154(b) by 0 days.

(21) Appl. No.: 13/940,896

(22) Filed: Jul. 12, 2013

(65) Prior Publication Data

US 2014/0017177 A1 Jan. 16, 2014

Related U.S. Application Data

(60) Provisional application No. 61/670,999, filed on Jul. 12, 2012.

(51) Int. Cl.

| *A61K 36/00* | (2006.01) |
| *A61K 36/36* | (2006.01) |
| *A61K 45/06* | (2006.01) |
| *A61K 31/198* | (2006.01) |
| *A61K 31/444* | (2006.01) |
| *A61K 36/185* | (2006.01) |

(52) U.S. Cl.
CPC .............. *A61K 36/36* (2013.01); *A61K 31/198* (2013.01); *A61K 31/444* (2013.01); *A61K 36/185* (2013.01); *A61K 45/06* (2013.01)

(58) Field of Classification Search
CPC ..................................................... A61K 36/36
See application file for complete search history.

(56) References Cited

PUBLICATIONS

Bajpai et al. (2008) Bioresource Technology 99, pp. 8903-8908.*
Agrawal et al. (2010) Drug and Alcohol Dependence 108: 49-55.*
Agrawal et al. (2012) Addiction, 107 (7): 1221-1233.*
Bossong et al. (2009) Neuropsychopharmacology 34, 759-766.*
Dani et al. (2001) Phamacology, Biochemistry and Behavior 70: 439-446.*
Ramo et al. (2012) Clinical Psychology Review 32: 105-121.*
West et al. (1987) British Journal of Addiction 82, 407-415.*
Rotter et al. (2012) Neuropycholobiology 66: 126-133.*
Website document entitled: "Dream Herbs: Silene capensis" (available at http://dreamherbs.com/herbal-products/silene-capensis). Dated Mar. 22, 2011. Downloaded from website May 4, 2015.*
Drugs—Forum, Cravings—Using Silene Capensis as an Aid During Cannabis Withdrawal Period, Cravings, http://www.drugs-forum.com/forum/showthread.php?t=182937, Oct. 14, 2014, pp. 1-3.

* cited by examiner

*Primary Examiner* — Chris R Tate
*Assistant Examiner* — Russell Fiebig

(57) ABSTRACT

A composition can include: silene extract; and a carrier having the silene extract. The composition can include an active agent, such as a pharmaceutical or a nutraceutical. The composition can be in a form of a solid, paste, gel, gum, or combination thereof. The carrier can facilitate retention in the mouth, chewing, sucking, holding in the lip next to the gums, or other non-liquid format. A method can provide an alternative to an activity that reduces desire to perform the activity, the method can include: administering to a subject in need thereof the composition having silene. The method can include administering the composition in an effective amount to treat one or more of smoking dependence, tobacco withdrawal symptoms, and tobacco dependence in the subject, wherein the activity is smoking.

7 Claims, No Drawings

SILENE CAPENSIS FOR INHIBITING CRAVINGS

CROSS-REFERENCE

This patent application claims priority to U.S. Provisional Application No. 61/670,999, filed Jul. 12, 2012, which provisional application is incorporated herein by specific reference in its entirety.

BACKGROUND

Tobacco is among the most chemically complex substances known, with tobacco and tobacco smoke containing more than 8,000 compounds. While nicotine is regarded as the principal addictive component in tobacco, a variety of other factors also are believed to contribute to tobacco addiction. For example, tobacco smoke has been reported to have a monoamine oxidase (MAO) inhibitory effect. MAO is an enzyme involved in the breakdown of dopamine, which is a pleasure-enhancing neurotransmitter. See J. S. Fowler et al., "Inhibition of Monoamine Oxidase B in the Brain of Smokers," Nature (Lond), 379 (6567):733-736 (1996); J. Stephenson, "Clues Found to Tobacco Addiction," Journal of the American Medical Association, 275 (16): 1217-1218 (1996).

In addition to nicotine, tobacco also contains the minor alkaloids nornicotine, anabasine, and anatabine. High doses of tobacco alkaloids are known to cause disadvantageous side effects. Nicotinic alkaloids have been reported to cause nausea, dizziness, gastrointestinal distress, and palpitations in high doses. Goodman and Gilman, The Pharmacological Basis of Therapeutics, $11^{th}$ Ed., pp. 232-233.

Nicotine replacement therapy (NRT) has become one of the most widely used techniques for treating smoking cessation. Some smoking cessation aids deliver nicotine via transdermal or transmucosal devices, which allow delivery of nicotine through the skin or mouth, respectively. U.S. Pat. No. 5,512,306 describes a smoking cessation aid in the form of an inclusion complex formed between nicotine and a cyclo compound such as polysaccharide. U.S. Pat. No. 5,525,351 discloses a saliva-soluble stimulant formed from a gel and nicotine.

Nicotine replacement therapy has had limited success in the treatment of cigarette addiction and as a means of reducing the level of consumption of cigarettes. Two of the significant disadvantages of NRT are, first, the therapy involves administering nicotine, a toxic and addictive substance. Second, many individuals who use tobacco, particularly smokers, experience an unpleasant taste (or "burn") when ingesting nicotine orally. Smokers also experience similar effects from using smokeless tobacco products and, as a result, their use as an alternative to cigarettes has met with limited success. It would be desirable to develop a non-nicotine product that would avoid the addictive attributes of nicotine as well as the unpleasant taste associated with consumption of nicotine-containing products and which would provide temporary relief from the desire to smoke.

SUMMARY

In one embodiment, a composition can include a silene capensis extract. The extract can be an aqueous extract obtained by aqueous extraction with an aqueous solution. The extract can be an alcoholic extract obtained by alcoholic extraction with an alcoholic solution, which may include ethyl alcohol.

In one embodiment, a composition can include silene capensis, anatabine, and a pharmaceutically acceptable vehicle, diluent, or carrier.

In one embodiment, a composition can include: silene capensis, anatabine, Yerba maté extract, and a pharmaceutically acceptable vehicle, diluent, or carrier.

In one embodiment, a composition can include silene capensis extract, anatabine, and Yerba maté extract.

In one embodiment, a composition can include silene capensis, threonine, and a pharmaceutically acceptable vehicle, diluent, or carrier.

In one embodiment, a composition can include silene capensis, and threonine.

In one embodiment, a composition can include silene capensis extract, and threonine.

In one embodiment, the anatabine is synthetic anatabine. The anatabine can be provided in the form of an extract of a plant selected from the group consisting of datura, mandrake, belladonna, capsicum, potato, nicotiana, eggplant, and petunia.

In one embodiment, a method of providing an alternative to cigarette smoking that reduces the desire to smoke comprising administering to a subject in need thereof the composition having the silene capensis. The subject can be a human.

In one embodiment, a method of treating at least one of smoking cessation, tobacco withdrawal symptoms, tobacco dependence, and weight loss in a subject comprising administering to a subject in need thereof the composition having silene capensis.

In one embodiment, a method of reducing cravings can include administering to a subject having a craving the composition having silene capensis. The craving can be for an activity, such as smoking, drinking, eating, or doing drugs or performing an additive activity. The craving can be for a substance, such as tobacco, nicotine, beer, wine, liquor, ethyl alcohol, food, or the like.

In one embodiment, a composition effective in the treatment of alcohol dependency or nicotine dependency or craving therefrom can include: silene capensis; an alcohol craving blocking component and/or a nicotine craving blocking component (e.g., can be same as alcohol craving blocking component); and an antidepressant component; each such component present in beneficially sufficient amount such that the combination is effective to minimize or obviate the nutritional, physiological and psychological conditions that result in alcohol dependency. The alcohol craving blocking component is chosen from the group of Kudzu and Rhodiola Rosea. The antidepressant component is chosen from the group of components consisting of St. John's Wort, 5-Hydroxytryptophanm SAMe, Melatonin and Taurine. The antidepressant component is chosen from the group of components consisting of St. John's Wort, 5-Hydroxytryptophanm SAMe, Melatonin and Taurine.

The silene capensis composition can further include an anti-anxiety component. The anti-anxiety component is chosen from the group of anti-anxiety components consisting of Vitamin B complex, Glutamine, Niacin, SAMe, Hops, Melatonin and Rhodiola Rosea.

The silene capensis composition can further include a blood sugar stabilizer component. The blood sugar stabilizer component is chosen from the group of blood sugar stabilizer components consisting of Niacin and Chromium Picolinate.

The silene capensis composition can further include an energizer component. The energizer component is chosen from the group of energizer components consisting of Glutamine and Taurine.

The silene capensis composition can include an organ repair component. The organ repair component being chosen from the group of organ repair components consisting of Glutamine, Milk Thistle, Niacin and Taurine.

In one embodiment, a composition for reducing a craving for a substance can include: silene capensis; a carrier; and 5-hydroxytryptophan.

In one embodiment, a silene capensis composition can include at least one of the following: Cinnamon, Copper, Coenzyme Q, *Ginko Biloba, Ginseng, Gymnema Sylvestre*, Manganese, Pantothenic Acid, Vanadium, Vanadyl Sulfate, Vitamin C, Vitamin E, Zinc.

In one embodiment, a method for reducing a craving for a craved substance or craved activity can include the steps of: administering a composition having silene capensis to a subject having the craving.

In one embodiment, a composition can include: silene extract; and a carrier having the silene extract. The composition can include optionally an active agent, such as a pharmaceutical or a nutraceutical. The composition can be in a form of a solid, paste, gel, gum, or combination thereof. However, liquids may also be used, such as to gargle, swish, or otherwise retain in the mouth for a period or to swallow. In one aspect, the carrier is not water. In one aspect, the carrier facilitates retention in the mouth, chewing, sucking, holding in the lip next to the gums, or other non-liquid format.

In one embodiment, a method of providing an alternative to an activity that reduces desire to perform the activity can include: administering to a subject in need thereof the composition having silene capensis. The method can include administering the composition in an effective amount to treat one or more of smoking dependence, tobacco withdrawal symptoms, and tobacco dependence in the subject, wherein the activity is smoking. In one aspect, the activity is eating and the composition is administered in an effective amount to reduce desire to eat. In one aspect, the activity is alcohol consumption and the composition is administered in an effective amount to reduce desire to consume alcohol. In one aspect, the reduced desire is compared to the desire without administration of the composition, and the administration is by mouth delivery.

In one embodiment, a method of reducing cravings can include: orally administering to a subject having a craving the composition having silene capensis. In one aspect, the craving is for an activity. In one aspect, the craving is for a substance. In one aspect, the substance is tobacco. In one aspect, the substance is nicotine. In one aspect, the substance is a beer, wine, or liquor. In one aspect, the substance is ethyl alcohol. In one aspect, the substance is food. In one aspect, the reduced craving is compared to the craving without administration of the composition. In one aspect, the method can include retaining at least a portion of the composition in the mouth for at least one minute, 2 minutes, 5 minutes, 10 minutes or up to 20 minutes. If in the form of a gum, the composition can be retained and chewed for the duration of time so that the craved activity or substance is not performed or consumed during retention of the composition in the mouth. Similarly, a sucker or other formulation configuration for mouth retention can be used so that the craved activity or substance is not performed or consumed while the composition is in the mouth. The craved activity or substance can be inhibited or avoided for up to 15 minutes, 30 minutes 45 minutes, 1 hour, or 2 hours post utilization of the composition or after the composition is removed from the mouth or swallowed. At some point, the craving will return and the composition (e.g., fresh or unused composition or previously used composition) can be used again. To facilitate use, the composition is in a form of a solid, paste, gel, gum, or combination thereof, and the subject chews the composition. The composition can be in an appropriate format for use. In some instance, a liquid for gargling or swishing and optionally swallowing can be used.

In one embodiment, the composition can include silene and an active agent. The silene can be any silene species or in any form or combination described herein. The active agent can be any pharmaceutical or nutraceutical, such as those described herein or known.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to compositions that include plant parts of silene capensis or extracts thereof, methods of manufacture, and methods of using the same. Other plants of the same silene genus can be used in place of or in addition to silene capensis such as silene undulate, silene capensis Otth, and/or melandrium undulatum (Ait.) Rohrb. which can be regarded by the Xhosa people as a sacred plant.

The compositions can include any part of the silene capensis plant, preferably the root. However, stem, stalk, leaves, flowers, fruit, or other portion thereof may be used. The methods of manufacture can include obtaining a plant part of silene capensis and obtaining an amount thereof and preparation of the composition having the same. The manufacture can also include preparing an extract thereof. The manufacture can also include combining a nutraceutically acceptable carrier thereof with the silene capensis. The method of use can include using the silene capensis composition in a therapeutic method for inhibiting, preventing, and treating cravings, such as cravings for consumption of anything. Particularly, the silene capensis composition can be used for treatment or inhibition of cravings for tobacco use, either smoking or smokeless. Additionally, the cravings that can be inhibited or treated can include cravings for alcohol, food, sex, drugs, or the like. In fact, any craving for consuming anything or performing any act can be inhibited with the silene capensis composition.

As used herein, a "cravings" includes great or eager desires, such as a yearning for something. One can crave activities, such as running, television viewing, exercise, eating, sleeping, smoking, drinking, or sex. One can crave substances, such as food, alcohol, tobacco, or the like.

As used herein, "craved substance" includes any smoke, tobacco, food or drink-related substance such as fatty foods or alcohol, as well as any drug-related substance including any prescription, non-prescription, and/or homeopathic composition provided in any suitable delivery formulation including oral, intravenous, and inhalation administrations. In one embodiment, a craved substance may be any food-type substance, and further includes any sweetened-food substance such as baked goods including cookies, brownies, pies, cakes, and the like, and any candy-based substance including hard candy, soft candy, chewable candy, gums, French fries, fast-food, and the like, and dairy-based products such as ice cream, yogurts, cheeses, chocolate milk, sweetened milk, and the like. As used herein, a food-type substance also includes any beverage-based substance including fruit and/or juice-based beverages, chocolate-based beverages including hot chocolate, alcoholic beverage, beer, wine, spirits, non-alcoholic beverage, carbonated beverages, sweetened beverages, non-sweetened beverages, and the like. In still further embodiments, the craved substance may be a drug-based substance including pain relievers, tranquilizers, depressants, sleep aids, tobacco substances, cocaine, marijuana, and the like. In still further embodiments, the craved substance can be tobacco products, either smoking or smokeless. Cigarettes are a prime example of craved substance.

As used herein, a "compulsion" can be described as a behavior which a person does compulsively—in other words, not because they want to behave that way, but because they feel they have to do so. Compulsions can be classified as cravings. When one feels compelled to perform an activity or consume a substance, that compulsion can be identified as a craving to perform that activity or consume that substance. Mental health professionals have identified signs of compulsive behavior in various disorders such as: Obsessive-compulsive disorder—obsessive, distressing, intrusive thoughts and related compulsions which attempt to neutralize the obsessions; and Drug addiction—a condition where a person takes a drug compulsively, despite potential harm to themselves, or their desire to stop. Here, alcohol, tobacco, or food can be a "drug." Performing activities, which may release endorphins, may also be considered a "drug." Herein, reducing, inhibiting, or treating a craving can reduce, inhibit, or treat a compulsion.

Compositions useful in relieving craving in nicotine habituated patients are provided that include an herbal component. The herbal component provides one or more herbal substances, such as silene capensis. The compositions are preferably in the form of silene capensis root, silene capensis root extract, silene capensis root powder, silene capensis liquids, silene capensis brews as well as chewing gum, tablets, capsules, or lozenges having or prepared from silene capensis or extract thereof.

The compositions containing silene capensis, powder thereof, or extract thereof can be efficacious for temporarily reducing general cravings. This can include reducing cravings for activities or substances in general.

In a primary embodiment, general silene capensis compositions, such as nutraceutical compositions, containing silene capensis powder or extract are efficacious for temporarily reducing the desire to smoke, reducing nicotine cravings, the treatment of smoking cessation, tobacco withdrawal symptoms, tobacco dependence, weight loss, and/or related disorders.

Embodiments of the present invention are directed to pure silene capensis compositions, such as raw root, powders thereof, or extracts thereof as well as combinations of substances with silene capensis for temporarily reducing the desire to perform an activity or intake a substance. In the primary embodiment, the present invention can reduce the craving to smoke and, in other contexts, reduce tobacco withdrawal symptoms, tobacco dependence, and/or other related disorders. More particularly, embodiments of the present invention are directed to compositions containing silene capensis in amounts that can be generally found in naturally occurring root product, powders, extracts, and foodstuffs and beverages in order to provide temporary relief from the craving.

The silene capensis can be consumed as described herein or in any way that silene capensis can be prepared for consumption. According to aspects of the present invention, the compositions are referred to a nutraceutical insofar as the ingredients of the compositions are obtained from or found in foodstuffs and/or beverages and in amounts generally found in naturally occurring foodstuffs and/or beverages. The ingredients can be obtained from or otherwise derived or extracted from silene capensis and added to foodstuffs or they can be synthetically prepared. For example, substances naturally found in silene capensis may be prepared synthetically or may be provided in the form of a silene capensis plant extract or powder.

Compositions containing silene capensis were unexpectedly found to be effective for temporarily reducing cravings for tobacco. Silene capensis may have been found as exhibiting MAO inhibition activity do to the biological of reducing cravings, such as reducing cravings for tobacco. As such, silene capensis may inhibit MAO activity. However, embodiments of the present invention are based on the surprising discovery that compositions containing silene capensis alone or in combination with components in amounts can be regarded as MAO inhibitory compositions that are efficacious for the temporary reduction of tobacco cravings and, in certain contexts, useful for facilitating smoking cessation, inhibiting tobacco withdrawal symptoms, inhibiting tobacco dependence or inhibiting other cravings or compulsions.

It has been found that compositions combining silene capensis are effective for the temporary reduction in cravings for tobacco products, and alleviation of tobacco withdrawal symptoms, while minimizing undesirable side effects associated with the administration of nicotine replacement therapy or the use of smokeless tobacco products.

In one embodiment, a composition comprises a silene capensis extract and optionally a pharmaceutically acceptable vehicle, diluent, or carrier. That is, the composition can be pure silene capensis extract or may optionally include a carrier.

In one embodiment, a method is provided for administering to a subject a composition containing silene capensis or silene capensis extract for the temporary reduction of tobacco cravings and, in certain contexts, for facilitating smoking cessation, inhibiting or treating tobacco withdrawal symptoms, inhibiting or treating tobacco dependence or inhibiting other cravings or compulsions.

The compositions may be prepared in a variety of formulations. For example, the compositions may be in the form of a beverage, a chew, a tablet, a capsule, a capsule having powder, a lozenge, or a gum.

In one embodiment, the compositions alternatively may be in the form of chewing tobaccos, snuffs, snus, and the like that have silene capensis or silene capensis extract. These compositions can be used to help associate the use thereof with a reduction or inhibition in craving the chewing tobaccos, snuffs, snus, and the like. This can inhibit a user from wanting to use the chewing tobaccos, snuffs, snus, and the like in the future, thereby inhibiting the craving therefor.

Additional inactive ingredients may be added to improve taste or stability of the compositions. Optionally, other components such as sweetening and flavoring agents may be added to improve edibility and improve compliance.

Optionally, the compositions may be provided in a time-release formulation to provide therapeutic effects over extended periods. Extended release formulations are known in the art. For example, swellable particles are taught in U.S. Pat. Nos. 5,582,837, 5,972,389, and 6,723,340. Polymer matrices are taught in U.S. Pat. Nos. 6,210,710, 6,217,903, and 6,090,411. Typical materials used for extended release formulations are the polymers poly(ethylene oxide) and hydroxypropyl methylcellulose. Tablet formulations for slow release are also described in U.S. Pat. No. 5,942,244.

In one embodiment, the silene capensis or silene capensis extract can be combined with anatabine to form a craving-reducing composition. The anatabine may be obtained from any suitable source, either as an extract or as synthesized anatabine. Synthetic anatabine is commercially available from several chemical suppliers. Anatabine may be prepared synthetically, such as via a benzophenoneimine pathway as described in co-pending application Ser. No. 12/729,346, filed Mar. 23, 2010, the disclosure of which is incorporated herein by reference in its entirety. Alternatively, anatabine may be obtained by extraction from tobacco or other plants, such as members of the Solanaceae family, such as datura, mandrake, belladonna, capsicum, potato, nicotiana, eggplant, and petunia.

In one embodiment, the silene capensis or silene capensis extract can be combined with Yerba maté extract or Yerba maté extract. The Yerba maté extract or Yerba maté extract can be obtained in any manner. The combination can be prepared into a composition as described herein.

In one embodiment, the silene capensis or silene capensis extract can be combined with Yerba maté extract and/or Yerba maté extract and anatabine. This three-component composition can be especially useful for inhibiting or treating cravings as described herein.

In one embodiment, a composition can include silene capensis or silene capensis extract and at least one of L-carnitine, acetyl L-carnitine and propionyl L-carnitine or the pharmacologically acceptable salts thereof is disclosed. This composition can be used as a therapeutic composition for suppressing withdrawal symptoms and cravings for alcohol in alcoholics, and as a dietary supplement, health food, medical food or nutraceutical for preventing the abuse of alcohol in substantially healthy subjects, particularly in young individuals. Also, this composition can be especially useful for inhibiting or treating cravings as described herein In one embodiment, a composition can include silene capensis or silene capensis extract and at least one of Kudzu and *Rhodiola*.

In one embodiment, a composition can include silene capensis or silene capensis extract and at least one of St. John's Wort (Hypericin), 5-Hydroxytryptophanm SAMe, Melatonin and Taurine.

In one embodiment, a composition can include silene capensis or silene capensis extract and at least one of Vitamin B complex, Glutamine, Niacin, SAMe, Hops, Melatonin.

A composition effective in the treatment of alcoholism can include silene capensis or silene capensis extract and one or more alcohol craving blocker components such as Kudzu and *Rhodiola Rosea*, and/or one or more antidepressant components such as St. John's Wort (Hypericin), 5-Hydroxytryptophanm SAMe, Melatonin and Taurine, and/or one or more anti-anxiety components such as Vitamin B complex, Glutamine, Niacin, SAMe, Hops, Melatonin and *Rhodiola Rosea*. The composition can include components chosen such that in combination they beneficially affect the nutritional, physiological and psychological deficiencies that combine to cause alcohol dependency. Also, this composition can be especially useful for inhibiting or treating cravings as described herein Accordingly, embodiments relate generally to the field of compositions and methods of use to treat addictive diseases, to inhibit cravings, tobacco use, and alcoholism or alcohol use. In one aspect, such compositions can include nutraceuticals, i.e., a product isolated or purified from foods or natural products, and generally sold in medicinal forms not usually associated with food and demonstrated to have a physiological benefit or provide protection against chronic disease, as opposed to pharmaceuticals, i.e. synthesized drugs. The compositions have nutritionally beneficial components that address specific deficiencies and/or address other nutritional, physiological or psychological concerns (such as for example depression, anxiety, unstable blood sugar levels, energy levels or organ problems) that in combination result in addictive diseases, to inhibit cravings, tobacco use, and alcoholism or alcohol use.

In a basic embodiment, the composition includes silene capensis or silene capensis extract and one or more alcohol craving blocker components, one or more antidepressant components, and/or one or more anti-anxiety components (i.e., anxiolytics), each component present in amount sufficient to beneficially minimize or obviate the nutritional, physiological and psychological conditions that in combination result in alcohol dependency. In addition to the above, alternative embodiments of the composition directed at specific needs can include individually or in combination blood sugar stabilizer components, energizer components and organ repair components.

The alcohol blocker component of the composition can include one or more components chosen from the group of components consisting of Kudzu (Daidzin) and *Rhodiola Rosea*, which composition can be used for inhibiting cravings for alcohol.

The antidepressant component of the composition can include one or more components chosen from the group of components consisting of St. John's Wort (Hypericin), 5-Hydroxytryptophanm SAMe, Melatonin and Taurine. The anxiolytic component of the composition can include one or more components chosen from the group of components consisting of Vitamin B complex, Glutamine, Niacin, SAMe, Hops, Melatonin and *Rhodiola Rosea*. The blood sugar stabilizer component of the composition can include one or more components chosen from the group of components consisting of Niacin and Chromium Picolinate. The energizer component of the composition can include one or more components chosen from the group of components consisting of Glutamine and Taurine. The organ repair component of the composition can include one or more components chosen from the group of components consisting of Glutamine, Milk Thistle (Silymarin), Niacin and Taurine. As noted, some of the component members address multiple deficiencies or problems. These types of components can be used with silene capensis or silene capensis extracts to inhibit or treat cravings.

In one embodiment, compositions can be configured for inhibiting general cravings or specific for inhibiting alcohol cravings, which compositions can include the following combinations comprising the listed components: (a) silene capensis and Kudzu and St. John's Wort; (b) silene capensis and Kudzu and Vitamin B complex; (c) silene capensis and Kudzu and St. John's Wort and Vitamin B complex; (d) silene capensis and Kudzu and 5-Hydroxytryptophan; (e) silene capensis and Kudzu and 5-Hydroxytryptophan and Vitamin B Complex; (f) silene capensis and Kudzu and Taurine; (g) silene capensis and Kudzu and Taurine and Vitamin B complex; (h) silene capensis and Kudzu and Melatonin; or (i) silene capensis and Kudzu and Melatonin and Vitamin B complex Daily effective dosage amount ranges for the components, the amounts being effective when given in combination as described to beneficially address the nutritional, physiological and psychological deficiencies that result in alcohol dependency and addiction, are as follows: silene capensis at any therapeutic amount where the amount can vary depending on the amount of active ingredient from silene capensis, such as from about 1 mg to 1 g, preferably from 25 mg to 500 mg, more preferably 25 mg to about 250 mg; Kudzu: from about 450 to 11,500 mg, preferably from about 1,350 to 4,100 mg, and most preferably from about 2,300 to 3,200 mg; St. John's Wort: from about 300 to 6,000 mg, preferably from about 600 to 4,700 mg, and most preferably from about 1,600 to 3,700 mg; Vitamin B complex: for each component present, from about 5 to 500 mg B1, from about 5 to 500 mg B2, from about 5 to 500 mg Niacinamide, from about 5 to 500 mg B6, from about 5 to 500 mcg B12, from about 5 to 500 mcg Folic Acid, from about 5 to 500 mcg Biotin, from about 5 to 500 mg Pantothenic Acid, from about 5 to 500 mg Choline Bitartrate, from about 5 to 500 mg Inositol and from about 5 to 500 mg Para-aminobenzoic Acid; preferably from about 100 to 400 mg B1, from about 100 to 400 mg B2, from about 100 to 400 mg Niacinamide, from about 100 to 400 mg B6, from about 100 to 400 mcg B12, from about 100 to 400 mcg Folic Acid, from about 100 to 400 mcg Biotin, from about 100 to 400 mg Pantothenic Acid, from about 100 to 400 mg Choline Bitartrate, from about 100 to 400 mg Inositol and from about 100 to 400 mg Para-aminobenzoic Acid; and most preferably from about 200 to 300 mg B1, from about 200 to 300 mg B2, from about 200 to 300 mg Niacinamide, from about 200 to 300 mg B6, from about 200 to 300 mcg B12, from about 200 to 300 mcg Folic Acid, from about 200 to 300 mcg Biotin, from about 200 to 300 mg Pantothenic Acid, from about 200 to 300 mg Choline Bitartrate, from about 200 to 300 mg Inositol and from about 200 to 300 mg Para-aminobenzoic Acid; 5-Hydroxytryptophan: from about 25 to 800 mg, preferably from about 100 to 500 mg, and most preferably from about 300 to 400 mg; Taurine: from about 50 to 50,000 mg, preferably from about 750 to 8,000 mg, and most preferably from about 3,000 to 5,000 mg; Melatonin: from about 0.5 to 15 mg, preferably from about 0.5 to 9 mg, and most preferably from about 3 to 5 mg; *Rhodiola Rosea*: from about 50 to 20,000 mg, preferably from about 400 to 3,000 mg, and most preferably from about 750 to 1,500 mg; SAMe: from about 50 to 2,400 mg, preferably from about 200 to 1,200 mg, and most preferably from about 400 to 800 mg; Glutamine: from about 500 to 8,000 mg, preferably from about 2,000 to 6,000 mg, and most preferably from about 2,000 to about 4,000 mg; Niacin: from about 100 to 3,000 mg, preferably from about 1,000 to 2,800 mg, and most preferably from about 1,800 to 2,400 mg; or Hops: from about 100 to 1500 mg, preferably from about 400 to 1,200 mg, and most preferably from about 600 to 1,200 mg.

It can be helpful for the components be provided in their most effective form, as many may be obtained on the market in forms that have reduced, ineffective or unavailable active ingredients, which are due to many factors, including but not limited to the time of harvest, the freshness of the component and storage temperature. In recent years the more popular components of those above have come to be marketed in what is referred to as "standardized" form, which means that the most active ingredient is artificially enhanced to approximate the amount or effectiveness of the active ingredient available in well-prepared fresh herbs or other source plants. The combined standardized form is often far more effective than just the accepted most active ingredients. The difference is commonly accepted to be the synergistic effects of known or unknown less important active ingredients. Thus, for certain components it is important to ascertain the true amount of the most well-known active ingredient, as opposed for example to the beneficial and effective amounts set forth above, which correlate to the estimated amount of natural fresh herbs.

However, silene capensis can be used in amounts depending on whether raw or extract. Also, the amount can be varied depending on the type of extract or method of extraction. As such, the amount of saline capensis can be varied in order to obtain the desired effect of inhibiting or treating cravings, such as tobacco cravings. The amount of silene capensis may then range from 1 microgram to 1 gram, and any amount therebetween. This amount can be a per use amount or a daily use amount. Most often, the silene capensis will be used in a per use manner to inhibit cravings on demand. When cravings occur, the silene capensis can be administered.

In accordance with one aspect of the present invention, a composition having silene capensis formulated to at least partially relieve cravings for a craved substance is provided. The composition includes silene capensis as a craving-reducing agent. Additionally, the composition can include silene capensis and 5-hydroxytryptophan. This novel composition may be useful in relieving cravings associated with various foods, especially foods higher in sugar content, various beverages, including alcoholic beverages, tobacco products as well as cravings for certain drugs, such as cocaine.

In accordance with a further aspect of the invention, a composition for facilitating weight loss is provided. As will be described in greater detail below, the composition includes various ingredients in combination with silene capensis and 5-hydroxytryptophan effective at reducing cravings and promoting weight loss. In various embodiments described hereinbelow, such ingredients include various chromium formulations, such as chromium piccoliate, in combination with a Vitamin B Complex, such as pyridoxyl-5-phosphate. In accordance with further exemplary embodiments, additional ingredients include *gymnema sylvestre*, ginger extract, green tea extract, *garcinia cambogia, ginko biloba*, cayenne pepper, cinnamon, cyanocobalmin, folic acid, Vitamin E, copper, amino acids, catalysts, co-factors, and the like.

In accordance with another aspect of the invention, a composition is provided wherein a craving-reducing agent is admixed into a carrier comprising a craved substance for consumption. The composition in accordance with this aspect of the invention promotes uptake of a craving-reducing agent. In one embodiment in accordance with this aspect of the invention, a craving-reducing agent including silene capensis and 5-hyroxytrptophan is admixed into a craved substance, such as, for example, hard candies, soft candies, chewable candies, and the like, for consumption. In accordance with this aspect of the invention, compositions and methods are provided to encourage uptake of a craving-reducing agent and decrease consumption of a craved substance by admixing the craving-reducing agent of silene capensis into a substance, or substance substitute, such as sugar-free candies, and the like.

In one aspect of the present invention, a composition useful in relieving cravings in a nicotine habituated patient who is abstaining from or reducing nicotine intake comprises an herb or an herbal extract providing a plurality of nicotine agonists, at least one of the nicotine agonists being silene capensis, and optionally anabasine in an amount of at least about 0.2 weight percent of the herb or herbal extract, the herb or herbal extract having from about 0 weight percent nicotine to trace levels of nicotine therein. The composition further includes an edible carrier (e.g. solid or liquid) for the herb or herbal extract.

A combination of nicotine agonists is silene capensis and anabasine and anatabine provided by flowers, dried leaves, stems, and/or roots, particularly of the Nicotiana glauca plant, or an herbal extract thereof. Suitable edible carriers include gums or binders (particularly for chewing gum formulations) and tableting agents (for tablet or lozenge formulation embodiments of the invention). The root of the silene capensis can be used.

Broadly, compositions of this invention are edible, that is to say, they are suitably formulated for oral use (e.g., chewing gum, tablets, lozenges, capsules, and the like). Regardless of the particular form, the compositions consist essentially of an herbal component that is derived from a plant or mixtures of plants having silene capensis and a quantity of anabasine and at least one other nicotine agonist, but with little or no nicotine. Among the plants from which the herbal anabasine component may be obtained are, for example, *Medicago sativa, Lupinus formosus, Solanum carolinense, Aniba coto, Zinnia elegans, Sophora pachycarpa, Verbascum songaricum, Priestleya elliptica, Priestleya tomentosa, Haloxylon persicum, Haloxylon salicornicum*, and *Nicotiana glauca*. Some species include quantities of both anabasine and nicotine, such as *N. glauca and N. debneyi* (with anabasine predominating).

An example of a plant for obtaining the herbal component is *N. glauca* (sometimes commonly called "tree tobacco"). This is a very wide-spread plant in the United States and grows at diverse places. It has been medicinally used as an analgesic poultice applied externally. Anabasine is the dominant alkaloid in *N. glauca* leaves. this can be mixed with silene capensis.

The herbal component of this invention will usually be provided by (or derived from) plant foliage (leaves and stems), although plant roots (e.g., such as silene capensis) can also be used also. Concentrations of silene capensis or anabasine in some plants are higher in roots than in leaves. The herbal component can be incorporated as dried plant parts or an extract therefrom. Herbal extracts are extracts of plant materials, such as a tincture of botanical materials, which typically are prepared by contacting botanical material with a solvent (British Herbal Pharmacopeia, Peter R. Bradley, Ed., British Herbal Medicine Association, 1983; and British Herbal Compendium, Peter R. Bradley, ed., British Herbal Medicine Association, 1992). The solvent, for example, can be aqueous or organic, or a combination thereof. Acceptable organic solvents include, but are not limited to, glycerin, propylene glycol or alcohol, or a combination thereof. The most preferred solvents are hydroalcoholic solvents as defined in British Herbal Pharmacopeia and Compendium.

Since a smoking cessation program may begin by gradual cessation of nicotine, followed by more complete, or by complete cessation of nicotine, inventive compositions may be formulated that have some nicotine (albeit in quantities substantially less than the silene capensis and optionally anabasine amount) in which case there are an expanded number of plant sources suitable as the precursor for the herb or herbal extract. It is believed that use of an herbal component with multiple agonists to provide the essential silene capensis component results in surprisingly improved properties and results. We do not presently know why the use of an herb or an herbal extract with silene capensis provides the surprisingly improved properties and results for treating patients in a smoking reduction or cessation program. Without being limited by theory, it may be that the essential silene capensis component serves as primary agonist and the one or more additional agonists, particularly such as the preferred anatabine, even when present in relatively small amounts, serves or serve as a co-agonist or co-agonists. Alternatively, it may be that there are multiple binding sites on the receptor.

In any event, use of silene capensis herbs or herbal extracts in accordance with this invention provides a mixture of complex ingredients. Since an agonist stimulates the receptor by stabilizing an active confirmation, and this stabilization can be achieved in many different ways depending upon the chemical nature of the ligand and on the structure of the receptor, the combination of agonists provided from a source of complex ingredients, such as the suitable herbs or herbal extracts of this invention, may achieve a stabilizing function through multiple interactions at different parts of the target receptor.

In compositions of this invention, the silene capensis content per recommended dose is in the range of between about 0.5 mg to about 10 mg, more preferably from about 2 mg to about 4 mg. Thus, for example, if a recommended daily dose is 8 tablets (as in chewing gum), then a patient could be receiving about 1-80 mg/day, more preferably 4-32 mg/day, of silene capensis.

In compositions of this invention, the anabasine content per recommended dose is in the range of between about 0.5 mg to about 10 mg, more preferably from about 2 mg to about 4 mg. Thus, for example, if a recommended daily dose is 8 tablets (as in chewing gum), then a patient could be receiving about 1-80 mg/day, more preferably 4-32 mg/day, of anabasine.

Compositions of the invention can have from only small, or trace, amounts of nicotine or no nicotine at all. Thus, the amount of nicotine per recommended dose will be from 0 wt. % to trace levels.

When formulated as tablets, lozenges, capsules, or chewing gum, it is contemplated that the silene capensis herbal component can be present in an amount from about 200 mg to about 600 mg dry weight, or about 50 mg to 400 mg liquid extract of the dry plant material (e.g., root). Such compositions will typically also include additional components such as a binder, a humectant, and flavoring agents such as sweeteners, artificial or natural fruit flavors, oils, and the like. Coloring may also be included.

Thus, in one embodiment, the composition is included in a chewing gum formulation. The formulations of chewing gum are conventional, and well known to those skilled in the art. For example, a carrier may be provided that may be mixed with the herbal component. Suitable carriers, particularly in formulating chewing gums, comprise arabic, guar, and natural rubber gums. Other typical components are sweeteners (sugar, saccharin, sorbitol, aspartame), flavoring agents (e.g., mints, fruits, spices), coloring agents, and the like.

For example, the chewing gum or solid carrier may be composed, in its basic formula, of ingredients such as sucrose, corn syrup, gum base, coloring and flavoring. Ingredients such as HSH (hydrogenated starch hydrolysate), sorbitol, xylitol, and/or isomalt can replace sucrose and corn syrup at different ratios. As an example of preparation, to a hot water jacketed stainless steel gum mixer equipped with sigma tangential blades rotating at 9-12 rpm with a 1:2 rotating ratio, molten gum base may be added at approximately 55-55° C., and corn syrup or HSH, added at room temperature in the desired amounts, and mixed until fully dispersed. When a homogeneous mix is obtained, sucrose or sorbitol, xylitol, or isomalt may be added, all in powder form, and mixed until fully dispersed. During the process of the addition of the powder material, the herbal component may be added. Color, flavoring, and any other ingredient deemed necessary for the particular formula may be added. The gummy mass is then discharged from the gum mixer and conveyed to the gum forming equipment.

Thus, for example, the solid portion or chewing gum used as a carrier for the herbal component may be composed of sucrose (10-80%, preferably 15-50%), corn syrup (5-60%, preferably 10-30%), gum base (10-90%, preferably 20-80%), sorbitol (10-60%, preferably 20-50%), hydrogenated starch hydrolysate (HSH) (5-60%, preferably 10-30%), hydrolyzed proteins (1-8%, preferably 1.5-3.0%), isomalt (10-80%, preferably 15-50%), xylitol (10-80%, preferably 15-50%), artificial sweeteners (0.2-2.0%, preferably 0.5-1.0%), natural sweeteners, coloring, and flavor ingredients—to appearance and taste. Additional ingredients may include other botanical extracts, gelatin, glycerin, starch and modified starches (1-7%, preferably 1.5-5.0%), these being used for the purpose of modifying texture and chewing properties of the gum as well as to enhance the release of nicotine agonists from the gum matrix. The texture and physical properties of the finished product are affected by the final form of the chewing gum, which can also be in sugar or sugar-free form. Such a chewing gum formulation may also include a liquid center in the gum. In such case, the herbal component, preferably in the form of an herbal extract in suitable solvent, may be incorporated into or serve as the liquid center.

In another embodiment, the silene capensis herb or herbal extract component of this invention is included in a tablet, capsule, or a lozenge for oral administration of the medication with local effects on the mouth and throat. Known tableting agents, binders, and the like as carriers may be used in such formulations. A lollipop configuration, which is essentially a lozenge with a stick, can also be useful. Buccal patches may also be useful.

Further, liquid preparations (where the carrier is a liquid) and emulsions of silene capensis are also contemplated for the inventive compositions.

An object of the present invention is to provide a composition for suppressing craving for smoking with high safety and no dependence such that there can be performed (1) suppression of craving for smoking in a situation where non-smoking is mandatory in the daily life; (2) prohibition or moderation of smoking intentionally (when unrestricted); and (3) complete elimination of a smoking habit. Another object of the present invention is to provide a method for prohibiting or moderating smoking comprising administering to an individual the composition comprising silene capensis.

As the form of the composition of the present invention, a food composition or a pharmaceutical composition is can be used, from the viewpoint of its suitability for the daily use.

The food composition of the present invention encompasses not only a food comprising silene capensis but also a food additive comprising silene capensis. In the case of making the food composition, silene capensis may be added to, for example, the following foods.

Specifically, silene capensis can be added to a solid food or a liquid food. The solid food is not particularly limited, and can include tablet confectioneries, candies, chocolates, gum, crackers, biscuits, cookies, paste products, processed soy products, mousse, jelly, yogurt, cold confectioneries, cake, bread and the like. The liquid food is also not particularly limited, and silene capensis may be added to a table luxury beverage such as fruit juice concentrates, reconstituted juice concentrates, fresh juices, mixed fruit juices, fruit grain-containing fruit juice, fruit juice-containing beverages, mixed fruit/vegetable juice, vegetable juice, carbonated beverages, soft drinks, mineral water, milk, milk beverage and coffee, or an alcoholic beverage such as Japanese sake, beer, wine, cocktails, shochu, and whiskey, or the like.

Among them, a preparation suitable for absorption of silene capensis via the oral mucosa is preferred. For instance, a solid food in the form which can be sustained in the mouth for a given length of time, such as a tablet confectionery, a candy or gum. For uses, the raw silene capensis root can be chewed and maintained in the mouth, such as between the gum and lips for buccal delivery. In the case of the solid food, silene capensis can be gradually released in the mouth. By that action, silene capensis is absorbed internally via mainly the oral mucosa. When silene capensis is absorbed via the oral mucosa, silene capensis would be transported into the brain more efficiently than the case through the portal system, whereby its action can be exhibited. On the other hand, when considering oral intake, since it may be difficult to use gum depending on the kind of an occupation and a situation of a workplace, the form of tablet confectionery or candy may be more preferable. With respect to these various forms, as those suitable for absorption via the oral mucosa, a dosage form sustainable in the mouth for at least three minutes when orally taken is preferred. Moreover, the size and the form are preferably those which would be difficult to chew down and swallow.

In the case of making the composition of the present invention into a pharmaceutical or nutraceutical composition, its form, which is based on known pharmaceutical compositions, may be any of solutions, suspensions, powders, solid molded products and the like without being particularly limited thereto. Therefore, the pharmaceutical or nutraceutical composition is provided as tablets (including not only general tablet but also troche and the like), capsules, powdered agents, granules, health care drinks and the like. The pharmaceutical or nutraceutical composition can also be used in combination with other medicaments.

Moreover, as in the case of the food composition, those suitable for absorption via the oral mucosa can be useful. Accordingly, from the viewpoint of absorbing silene capensis internally without mediating portal system, as the form of the raw root, nutraceutical or pharmaceutical composition of the present invention, tablets, especially troche or a sublingual tablet, can be used. The sublingual tablet is not particularly limited, as long as the tablet can be placed under the tongue. It is desirable that the tablet preferably disintegrates in three to six minutes, whereby silene capensis can be released to sublingual mucosa rapidly. The tablet can be substituted with a capsule having silene capensis in powder or extract form. The means for disintegration is not particularly limited, and may follow a conventional method. By the use of the sublingual tablet or capsule, silene capensis is absorbed via sublingual mucosa and can be efficiently transported into the brain, so that the sublingual tablet or capsule is especially suitable for the treatment of acute withdrawal symptoms or the treatment of transient nicotine cravings.

A process for preparing the composition of the present invention is not particularly limited, and there can be used general processes for preparation of a food and a medicament such as a process of powder-mixing silene capensis and other raw materials; a process of dissolving silene capensis and other raw materials in a solvent to give a mixed solution; and a process of freeze-drying the mixed solution; a process of spray-drying the mixed solution. For example, a pharmaceutical composition can be prepared by mixing silene capensis with a vehicle, a carrier, a binder, a stabilizer and the like, which are known in the art.

By the use of the silene capensis composition of the present invention, there can be performed, for instance, (1) the suppression of craving for smoking in a situation where non-smoking is mandatory in the daily life. For an individual having a smoking habit who does not wish to eliminate the habit of smoking, it may be very difficult to quit smoking for a given period of time, whether short or long. The situation where nonsmoking is mandatory includes, for example, the situation during the use of public transportations such as air planes and the situation in a hospital. In these cases the craving for smoking can be suppressed efficiently by the use of the composition of the present invention so that smoking can be stopped without causing any problems. However, the suppressive action may be transient or not persistent unnecessarily for a long period of time, and smoking can be restarted easily once the period of time where nonsmoking is mandatory has passed. Such a flexibility of suppressing the craving for smoking and restarting smoking is very excellent aspect as compared to the suppression of the craving for smoking by conventional nicotine substitute such as nicotine pad which may unnecessarily sustain the suppressive effect for the craving for smoking. Particularly in recent years, there is an increase in a situation where nonsmoking is mandatory along with the progress of understanding about harmful action of cigarette consumption and nicotine intake accompanied therewith, so that the embodiment of the use of the composition of the present invention mentioned above is especially preferred.

Moreover, there can be performed (2) prohibition or moderation of smoking intentionally (when unrestricted) by using the composition of the present invention. When an individual having a habit of smoking who does not wish to eliminate the habit tries to stop or moderate smoking under a direction of a physician, when an individual tries to stop smoking during the contact with an infant, or the like, the craving for smoking can be suppressed efficiently by using the composition of the present invention, so that smoking can be stopped or moderated without causing any problems. In addition, in the same manner as mentioned above, in a case where intentional prohibition or moderation for smoking is no longer necessary, smoking cigarettes can be restarted at once.

Further, there can be performed (3) complete elimination of a smoking habit by taking the silene capensis composition of the present invention continuously. It is said that there are generally a few individuals having confidence about quitting smoking among smokers who are starting to stop smoking. This is especially true when an individual had given up on quitting smoking in some of past challenges due to painful withdrawal symptoms after starting quitting smoking. However, since the craving for smoking can be suppressed efficiently by using the composition of the present invention, nonsmoking can be continued without causing any problems, and finally, the smoking habit can be completely eliminated.

Moreover, by using the composition under the appropriate instruction or counseling for quitting smoking, a further effect can be expected. Hitherto, in the instruction or the like, nicotine preparations such as nicotine gum and nicotine pad have been used as anti-smoking supplement. However, nicotine is highly toxic and is contraindicated in individuals with unstable angina, individuals with myocardial infarction, gravida, women who are possibly pregnant and the like. The above-mentioned anti-smoking supplement should be prescribed for the purpose that an individual who intends to stop smoking may use it by himself under a proper direction. If another individual uses the anti-smoking supplement, it is not necessarily safe. Particularly, in the case of passing the anti-smoking supplement to the contraindicative individual by hand-over, there has been a possibility of causing a situation with risk. Moreover, a nicotine preparation serves as a temporary substitute of source of nicotine, which had been taken from cigarettes, so that dependence to the nicotine preparation may take place.

Since the silene capensis used in the composition of the present invention is completely safe component as mentioned below and has no possibility of silene capensis dependence, an addictive smoker can eliminate the smoking habit safely and effectively by the use of the composition under the direction for quitting smoking. In fact, test populations have not reported any dependence on silene capensis while also reporting that the cravings, such as for tobacco and alcohol, have been significant reduced after consumption. The use of small amounts of silene capensis allows for the craving to return, and the substance being craved can be consumed, if desired.

As described above, by the use of the silene capensis composition of the present invention, since withdrawal symptoms caused by prohibition or moderation of smoking can be prevented, alleviated or eliminated, the above-mentioned various embodiments of use can be made.

Further, the present invention provides a method for prohibiting or moderating smoking, comprising administering to an individual (human) a composition comprising silene capensis. In the method, the use of the composition of the present invention is preferred. An effective dose of silene capensis in order to obtain the desired effect of the present invention in the above-mentioned embodiment of use of the composition of the present invention is, generally, preferably from 0.1 to 50 mg/kg weight per day, more preferably from 0.5 to 20 mg/kg weight, still more preferably from 1 to 20 mg/kg weight, especially preferably from 4 to 20 mg/kg weight.

The timing of using the silene capensis composition of the present invention is not particularly limited. For instance, the composition may be previously administered when withdrawal symptoms are presumed to be caused by prohibition or moderation for smoking, or may be administered during occurrence of withdrawal symptoms. In a more specific embodiment, when a smoker wishes to temporarily treat withdrawal symptoms, the composition is administered to the smoker before or during the experience of withdrawal symptoms, the smoker being preferably a smoker who cannot help smoking during cigarette- or nicotine-deficient state for a long period of time, for instance, a smoker who has a habit of smoking within fifteen minutes from the point of waking. The smoker is administered in an effective dose per dosage of the silene capensis sufficient to suppress the craving for smoking, for instance, upon waking, which is preferably from 0.02 to 10 mg/kg weight, more preferably from 0.2 to 10 mg/kg weight, still more preferably from 0.8 to 10 mg/kg weight. On the other hand, when a smoker wishes to completely eliminate the smoking habit, it is desirable to administer an effective dose per dosage of the silene capensis sufficient to suppress the craving for smoking preferably for at least three hours or so, more preferably for five hours or so, for instance, upon beginning of the craving for smoking, which is preferably from 0.02 to 10 mg/kg weight, more preferably from 0.2 to 10 mg/kg weight, still more preferably from 0.8 to 10 mg/kg weight.

However, since there are differences (e.g. age, gender) between individuals in a level of smoking habit or withdrawal symptoms, the dosage of silene capensis in the present invention is not particularly limited to the above range. The dosage of silene capensis is may be properly adjusted depending upon each smoker's state and a desired effect level. Also, the number and interval of administration can be properly selected.

Further, as another embodiment of the present invention, the present invention provides use of silene capensis for preparing a medicament for preventing, alleviating or eliminating withdrawal symptoms caused by prohibition or moderation of smoking.

The silene capensis composition of the present invention is based on action for suppressing the craving for smoking that has been found for silene capensis for the first time.

In one embodiment, the silene capensis can be mixed in a plant part mixture, powder, extract or nutraceutical or smokable substitute with one or more of the following: Damiana, lion's tail (*leonotis leonurus*), mugwort, blue-lotus (*nympaea caerulea*) skullcap, Siberian motherwort (other motherwort), pink lotus (*nelumbo nucifera*), amanita, shredded ayahuasca, woodrose seeds, blue lotus petals, kratom extract powder, kratom leaves, prickly poppy, hops, salvia, salvia leaves, salvia extract, sinichuichi foliage. white lotus and amanita muscaria mushrooms (e.g., psychedelic effect).

In one embodiment, the silene capensis can be mixed in a plant part mixture, powder, extract or nutraceutical or smokable substitute with one or more of the following substances (with effect or use identified): amanita; clove (e.g., sexual function) or insect repellent, (less than 10%); asafetida—insect repellent, cough inhibitor; borage—depression aid, relaxant, sleep aid, sooth cough; California poppy—sedative; romneya coulteri; romneya trichocalyx; cardamom—mint smoke; catnip—minty, headache, sleep aid, indigestion, insect repellent, relaxant; celandine—sedative; poppywort (also known as *stylophorum*, celandine poppy, wood poppy, or yellow poppy)—*Stylophorum lasiocarpum, Stylophorum sutchuenense*; chamomile—relax; chia—energy and endurance; chickweed—stamina, reduce fever, energy; chrysanthemum—energy, improve senses; cinquefoil—inhibit bleeding; club moss—upset stomach, joint pain relief; coltsfoot—cough suppresent; geranium genus; dandelion—joint pain, diuretic, devils claw—appetite stim; devils club—mind enhancer, American *ginseng*; dong quai—sedative; *ginkgo*—alert focus improve blood flow, sexualilty; *ginseng*—appetite; gotu kola—antianxiety; kava kava root—feel good and tranquility; lemon grass—sedative; marjoram—relaxant tranquilizer; mugwort—visual and relaxant, sleep; rosemary—improve mental wellbeing; skullcap—tranquilizer sedative; valerian root—relaxation and antianxiety, and the like.

In one embodiment, silene capensis can be combined with glutamine and used as described herein.

EXPERIMENTAL

Many years ago Subject A used to make up their own mixes of different herbs for smart drugs and experimented with different combinations that worked better together or worked better when taken at different times of the day. Subject A tried different herbs, and in doing research come across silene capensis (xhosa) for vivid/lucid dreaming. Subject A decided to try some silene capensis, and then tried it a few times, usually at night. The recommendation was to use a blender and water with the plant's root and sip at the froth. Sipping at the froth was supposed to help with any nausea. Subject A found that chewing at a small piece of the root and putting it under the gum when I went to sleep didn't lead to much if any noticeable nausea.

One night in mid-November 2011, Subject A was hanging out with Subject B in his basement entertainment room drinking beers and talking. Subject B was giving Subject A flack about smoking, and eventually came up with a bet where Subject B would quit drinking and Subject A would quit smoking. We'd see who could go the longest. After some debate of the rules, it was decided that we would both go cold turkey starting the following day. Nicotine replacement (nicotine gum, etc.) counted as nicotine and if Subject A used it, Subject A would lose the bet. Subject A tried some different mixes of herbs to see if anything would help. Subject A had a mix of *Ginseng*/Gotu Kola/*Ginko* along with choline/inositol as well as bacopa, glutamine, and the silene capensis.

What was really surprising though was how much the silene capensis helped reduce the cravings for smoking tobacco. It really took the edge off the cravings. Subject A used the same technique by putting a small piece of silene capensis root in the mouth near the gum for buccal delivery. The silene capensis root would be about half the thickness of a pencil and as long as the tip of an adult index finger. When saliva had wet the root, Subject A would break it with teeth into several small strands and put it under the gum. Subject A used it through the day. The effects would wear off and the medicine taste would go away after a couple of hours. Subject A would chew on the root lightly again to expose new surfaces of the root and put it under the gum. Subject A repeated this process until it seemed like the silene capensis root was up and then try another. Sometimes it did seem like there was a noticeable effect on my stomach. It helped if Subject A avoided swallowing the saliva/capensis juices.

Subject A continued using the silene capensis root for many days. The withdrawal effects were most pronounced over the first 3-4 days. Subject A did try some lobelia (indian tobacco), and it was really helpful with the cravings. Silene capensis definitely helpful in reducing cravings.

Subject B was administered silene capensis root after requesting a beer and having the craving for beer. After administering the silene capensis root as described for Subject B, Subject B forgot to drink the beer. Subject B described having a significant reduction in desire or craving to drink the beer. Subject B was able to drink the beer after a period of time.

Subject C was administered silene capensis root after requesting a beer and having the craving for beer. After administering the silene capensis root as described for Subject C, Subject C decided against drinking the beer. Subject C described having a significant reduction in desire or craving to drink the beer and almost felt nauseous when offered the beer again. The craving for beer being completely removed from Subject C, and the beer being left unconsumed.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. A method for reducing a craving for smoking tobacco, the method comprising:
   orally administering to a subject in need thereof a composition comprising:
      an effective amount of a Silene capensis extract; and
      a suitable carrier.

2. The method of claim 1, wherein the orally administered composition is in an amount effective to treat one or more of smoking dependence, tobacco withdrawal symptoms, and/or tobacco dependence in the subject.

3. The method of claim 1, wherein the subject's craving is reduced compared to the subject's craving without administration of the composition.

4. The method of claim 1, wherein the composition is designed to be retained in the subject's mouth for at least one minute during administration of the composition to the subject.

5. The method of claim 1, wherein:
   the composition administered to the subject comes in contact with saliva of the subject during oral administration of the composition to the subject; and
   the saliva of the subject includes water.

6. The method of claim 1, wherein the composition is in a form of a solid, paste, gel, gum, silene root, and/or combination thereof.

7. A method of reducing a subject's withdrawal symptoms associated with nicotine intake and/or the subject's desire to intake nicotine, the method comprising:
   orally administering a composition to a subject in need thereof a composition comprising:
      an effective amount of a Silene capensis extract; and
      a suitable carrier,
   wherein the administered composition reduces the subject's desire to intake nicotine in the future and/or reduces the withdrawal symptoms
      of the subject due to prior intake of the nicotine over an amount of time.

* * * * *